(12) United States Patent
Bartholomew et al.

(10) Patent No.: US 12,370,360 B2
(45) Date of Patent: Jul. 29, 2025

(54) FLEXIBLE SHEET FOR NEUROMUSCULAR STIMULATION

(71) Applicant: Battelle Memorial Institute, Columbus, OH (US)

(72) Inventors: John Bartholomew, Hilliard, OH (US); Jeffrey Friend, Grove City, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 18/093,415

(22) Filed: Jan. 5, 2023

(65) Prior Publication Data

US 2023/0149705 A1    May 18, 2023

Related U.S. Application Data

(62) Division of application No. 16/856,066, filed on Apr. 23, 2020, now Pat. No. 11,571,564, which is a division of application No. 15/612,894, filed on Jun. 2, 2017, now Pat. No. 10,695,564.

(60) Provisional application No. 62/344,650, filed on Jun. 2, 2016.

(51) Int. Cl.
| | | |
|---|---|---|
| *A61N 1/04* | (2006.01) | |
| *A61N 1/36* | (2006.01) | |
| *B29C 39/10* | (2006.01) | |
| *A61B 5/296* | (2021.01) | |
| *B29L 31/00* | (2006.01) | |

(52) U.S. Cl.
CPC ......... *A61N 1/0496* (2013.01); *A61N 1/0452* (2013.01); *A61N 1/0476* (2013.01); *A61N 1/36031* (2017.08); *B29C 39/10* (2013.01); *A61B 5/296* (2021.01); *B29L 2031/753* (2013.01)

(58) Field of Classification Search
CPC .. A61N 1/0496; A61N 1/0452; A61N 1/0476; A61N 1/36031; A61N 1/36003; A61N 1/0436; A61N 1/044; A61N 1/0448; A61N 1/0456; A61N 1/0468; A61N 1/0534; A61N 1/0551; A61N 1/0558; B29C 39/10; A61B 5/296; A61B 5/6868; A61B 5/6828; A61B 2505/09; A61B 2562/0209; A61B 2562/0219; A61B 5/37; A61B 5/372; A61B 5/395; A61B 5/4041; A61B 5/4836; A61B 5/6802; A61B 5/6824; B29L 2031/753; B29K 2021/00; B29K 2075/00; B29K 2083/00
See application file for complete search history.

(56) References Cited

U.S. PATENT DOCUMENTS 5,068,001 A * 11/1991 Haussling ............... B29C 70/08
                                                                181/290
7,148,221 B2   12/2006 Doherty et al.
7,337,012 B2    2/2008 Maghribi et al.
(Continued)

*Primary Examiner* — Carl H Layno
*Assistant Examiner* — Anh-Khoa N Dinh
(74) *Attorney, Agent, or Firm* — Susanne A. Wilson; Frank Rosenberg

(57) ABSTRACT

A flexible sheet for neurostimulation is described having a flexible non-conductive substrate matrix in which electrodes are embedded along a lower surface. Electrically conductive wires extend from the electrodes through the flexible substrate to another exterior surface of the substrate. Methods of making the flexible sheet and making a device using the flexible sheet are also disclosed.

17 Claims, 9 Drawing Sheets

(56) References Cited

U.S. PATENT DOCUMENTS

| | | | |
|---|---|---|---|
| 7,760,082 B2 * | 7/2010 | Wong | A61B 7/00 |
| | | | 600/528 |
| 8,209,023 B2 | 6/2012 | Zhou et al. | |
| 8,712,538 B2 | 4/2014 | Greenberg et al. | |
| 9,018,532 B2 | 4/2015 | Wesselmann et al. | |
| 9,884,178 B2 | 2/2018 | Bouton et al. | |
| 10,426,945 B2 | 10/2019 | Tyler et al. | |
| 10,765,859 B2 | 9/2020 | Bouton et al. | |
| 2003/0097166 A1 * | 5/2003 | Krulevitch | A61N 1/0543 |
| | | | 607/116 |
| 2009/0235739 A1 * | 9/2009 | Morris Bamberg | A43B 3/34 |
| | | | 702/141 |
| 2013/0333094 A1 * | 12/2013 | Rogers | A61B 34/76 |
| | | | 340/407.1 |

* cited by examiner

FLEXIBLE SHEET FOR NEUROMUSCULAR STIMULATION

RELATED APPLICATION

This application is a divisional of U.S. patent application Ser. No. 16/856,066 filed Apr. 23, 2020, now U.S. Pat. No. 11,571,564, which is a divisional of U.S. patent application Ser. No. 15/612,894 filed Jun. 2, 2017, now U.S. Pat. No. 10,695,564, and claims priority to U.S. Provisional Patent Application Ser. No. 62/344,650, filed Jun. 2, 2016.

INTRODUCTION

The present disclosure relates to flexible sheets that can be used in systems, methods and devices for neuromuscular stimulation, sensing, and recording. Generally, such systems are used to receive thought signals indicative of an intended action and provide electrical stimulation to nerves and/or muscles to effectuate the intended action, thereby bypassing or assisting a damaged or degenerated region/pathway of the nervous system. The flexible sheets of the present disclosure can be used to make neuromuscular stimulation cuffs, also referred to herein as "neural sleeves," which deliver stimulation to restore movement to parts of the body not under volitional control due to damaged or degenerated neural regions/pathways from brain or spinal cord injury, stroke, nerve damage, motor neural disease, and other conditions or injuries. The system can also be used in a patient that has some local neural or muscle degeneration for therapeutic or rehabilitation purposes.

Transcutaneous neurostimulation cuffs place electrodes on the surface of the skin. Because the electrodes are placed on the surface of the skin, rather than below it as in subcutaneous cuffs, stimulation often can better target skeletal muscle tissue or muscle groups, rather than peripheral nerves located deeper under the skin. Muscular stimulation may be preferable to stimulating major peripheral nerves, e.g. ulnar, median, radial nerves, as stimulating these nerves may cause a patient to feel a tingling sensation and it is more difficult to effect the desired movement. By increasing the number and layout of electrodes in a neuromuscular cuff, similar to the direction taken with implanted nerve cuff designs, current generation neuromuscular stimulation cuffs have been able to selectively stimulate individual muscles or muscle groups and achieve finer movements such as individual finger flexing and extension.

Flexible-like transcutaneous cuffs have been developed which fit around a human appendage such as a forearm to control the wrist or fingers. These flexible cuffs may include sensors which record muscle activity, or electromyography (EMG) signals, and stimulate in response to the EMG signals. Thin film technologies have also become important in the development of functional electrostimulation (FES) devices. Devices incorporating thin film technology are often based on a polyimide substrate covered by a chromium, gold, or platinum film.

Current transcutaneous neuromuscular stimulation electrodes (or patches) present many limitations. Such neuromuscular patches are typically large (several cm across or more) and have a single electrode (conductive surface). This does not allow selective stimulation of small muscles segments for fine wrist and finger control.

It would be desirable to provide improved devices for neuromuscular stimulation. Flexible sleeves with multiple small electrodes would allow programmable spatial stimulation patterns, which is highly desirable when attempting to restore complex muscular movements through neuromuscular stimulation.

BRIEF DESCRIPTION

The present disclosure relates to flexible sheets containing electrodes embedded within or upon a flexible substrate. The substrate can be a non-conductive elastomeric polymer, or could be a fabric. These flexible sheets can be used to make a neuromuscular stimulation device (i.e. "neural sleeve") which can be used to stimulate a damaged region/pathway of the nervous system and cause movement of a limb (e.g. arm or leg).

Disclosed in various embodiments are flexible sheets, comprising: a non-conductive, flexible substrate; a plurality of electrodes embedded within the flexible substrate; and electrically-conductive wires running through the flexible substrate from a common exterior surface of the flexible substrate to each electrode.

The electrodes may be arranged such that the flexible sheet has a constant electrode density.

The plurality of electrodes can be arranged in a plurality of rows. Each row of electrodes can be connected to common electrically-conductive wires or individually isolated.

The flexible sheet may comprise a top surface, a bottom surface opposite the top surface, and a plurality of side surfaces; wherein the plurality of electrodes is located on the bottom surface; and wherein the wires extend to one of the side surfaces.

Each electrode may comprise a contact surface made of a conductive polymer or a metal. Each electrode may further comprise a charge dispersing plate between the contact surface and the electrically-conductive wire. Each electrode may further comprise a conduction enhancer on an exterior surface thereof.

In some embodiments, the flexible sheet further comprises a sensor embedded within the substrate. The sensor may be an accelerometer. The flexible sheet may alternatively further comprise a label printed upon an exterior surface of the flexible sheet.

The substrate may be a non-conductive polymer. Insulating ceramic material can be dispersed throughout the flexible substrate. The electrically-conductive wires can be bare, or can be insulated.

The flexible sheet may further comprise a mechanical fastener embedded in the substrate, for holding the flexible sheet in the form of a sleeve. Alternatively, the flexible sheet may further comprise a low-tack adhesive on an exterior surface of the flexible sheet for holding the flexible sheet in the form of a sleeve.

Also disclosed herein are flexible sheets, comprising: a fabric substrate; a plurality of conductive components on a bottom surface of the fabric substrate; and a plurality of non-conductive components on the bottom surface of the fabric substrate. The plurality of conductive components and the plurality of non-conductive components can be printed, deposited, or sewn onto the fabric substrate. The flexible sheet may further comprise wires woven into the fabric substrate.

Also disclosed herein are systems for muscular neurostimulation, comprising: an inner sleeve formed from the flexible sheet; and a compression sleeve surrounding the inner sleeve.

In another aspect, the invention provides a flexible sleeve for neuromuscular stimulation, comprising: a plurality of conductive wires that are each connected to an electrode; a non-conductive elastomeric matrix in which the wires and electrodes are embedded; a sensor (such as an accelerometer) embedded in the elastomeric matrix; wherein the electrodes are disposed along a bottom surface of the sleeve that contacts a subject's skin when the sleeve is worn. In some preferred embodiments, a fabric is embedded in the elastomer (substrate).

In a further aspect, the invention provides a method of making a flexible sheet, comprising: in a mold, placing conductive wires in connection with electrodes or contacts for electrodes; adding an elastomer precursor into the mold to encase the wires and electrodes or contacts for electrodes; and curing the elastomer precursor to create the flexible sleeve with embedded wires and electrodes or contacts for electrodes. In some embodiments, after the elastomer is added to the mold; further comprising a step of making electrodes by placing a conductive polymer in contact with the contacts for electrodes. Conductive particles can be added to the uncured elastomer to make the electrodes. The step of making electrodes may comprise depositing a precursor for a conductive polymer in contact with the contacts for electrodes, and, optionally, the conductive polymer is colored differently from the elastomer that makes the sleeve. A fastener can embedded in the elastomer for closing the sleeve.

In another aspect, the invention provides a method of making a custom-fit, flexible sleeve for neuromuscular communication, comprising: providing a flexible sheet comprising a plurality of conductive wires that are each connected to an electrode; a non-conductive elastomeric matrix in which the wires and electrodes are embedded; a sensor embedded in the elastomeric matrix; wherein the electrodes are disposed along a surface of the sheet; and wherein the wires connect at the same side of the sheet; and cutting the sheet to fit an individual patient such that the electrical connections from the side of the sheet to the electrodes are not disrupted.

Disclosed in further embodiments are methods for fitting a neuromuscular stimulation device to a patient, comprising cutting a flexible sheet to a size selected to match a treatment location on the patient; and joining opposing edges of the flexible sheet together.

These and other non-limiting aspects of the present disclosure are discussed in more detail below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
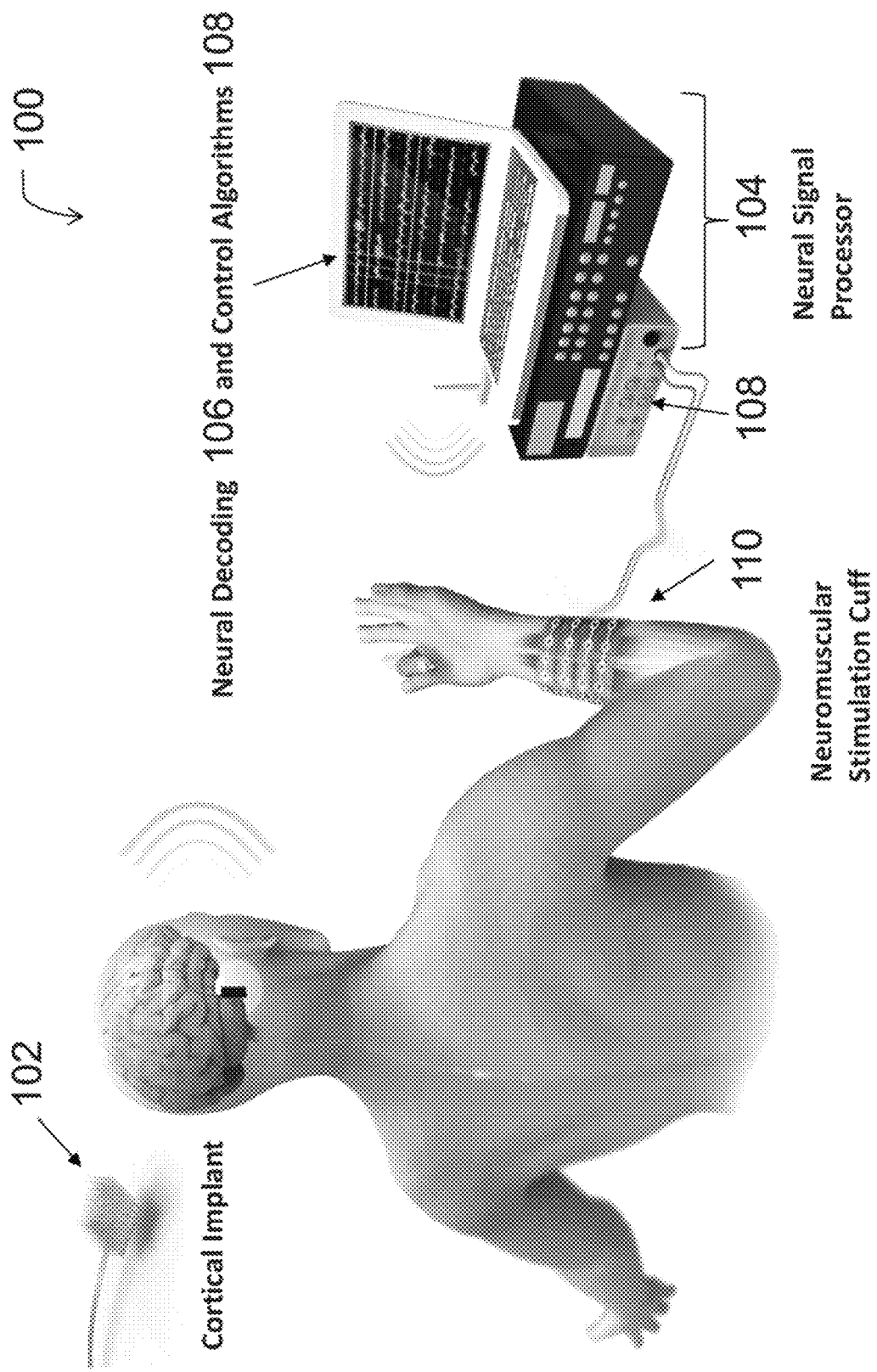
FIG. 1 is an overview diagram of one embodiment of a system for thought-controlled neuromuscular stimulation.

A more complete understanding of the processes and apparatuses disclosed herein can be obtained by reference to the accompanying drawings. These figures are merely schematic representations and are not intended to indicate relative size and dimensions of the assemblies or components thereof.

Although specific terms are used in the following description for the sake of clarity, these terms are intended to refer only to the particular structure of the embodiments selected for illustration in the drawings, and are not intended to limit the scope of the disclosure. In the drawings and the following description below, it is to be understood that like numeric designations refer to components of like function.

With reference to FIG. 1, a system for thought-controlled neuromuscular stimulation may include a cortical implant 102 implanted into the cerebral cortex region of the brain. The cortical implant 102 in one embodiment includes a microelectrode sensing array, as depicted in FIG. 1. The microelectrode sensing array includes multiple channels (e.g. 96 channels) and may be wired to an amplifier which further amplifies signals received by the microelectrode array. The cortical implant 102 records "brain waves," more particularly neural signals which are representative of a varied set of mental activities. Neural signals include electrical signals produced by neural activity in the nervous system including action potentials, multi-unit activity, local field potential, Electrocorticography (ECoG), and EEG. These neural signals are sent wirelessly or, alternatively, through a wired connection, from the cortical implant 102 to a receiver on a neural signal processor device 104 for processing of the neural signals. In another embodiment, a scalp based interface, headset, or other sensor 102 picks up electroencephalogram (EEG) signals and sends them to the receiver on the neural signal processor device 104.

The neural signal processor 104 may include a processor including neural decoding algorithms and/or control algorithms 108. These algorithms 108 allow for a received neural signal input to be decoded and subsequently re-encoded for use in neuromuscular stimulation. For example, a received neural signal may be isolated to predict arm and/or hand movements a patient is thinking about. The neural signal processor 104 may also include an oscilloscope or other signal waveform viewing and/or manipulation device. The neural signal processor also preferably includes an isolated pulse stimulator which receives a processed signal and generates a pulse signal for use in neuromuscular stimulation by an attached neuromuscular stimulation cuff 110.

Figure 2:
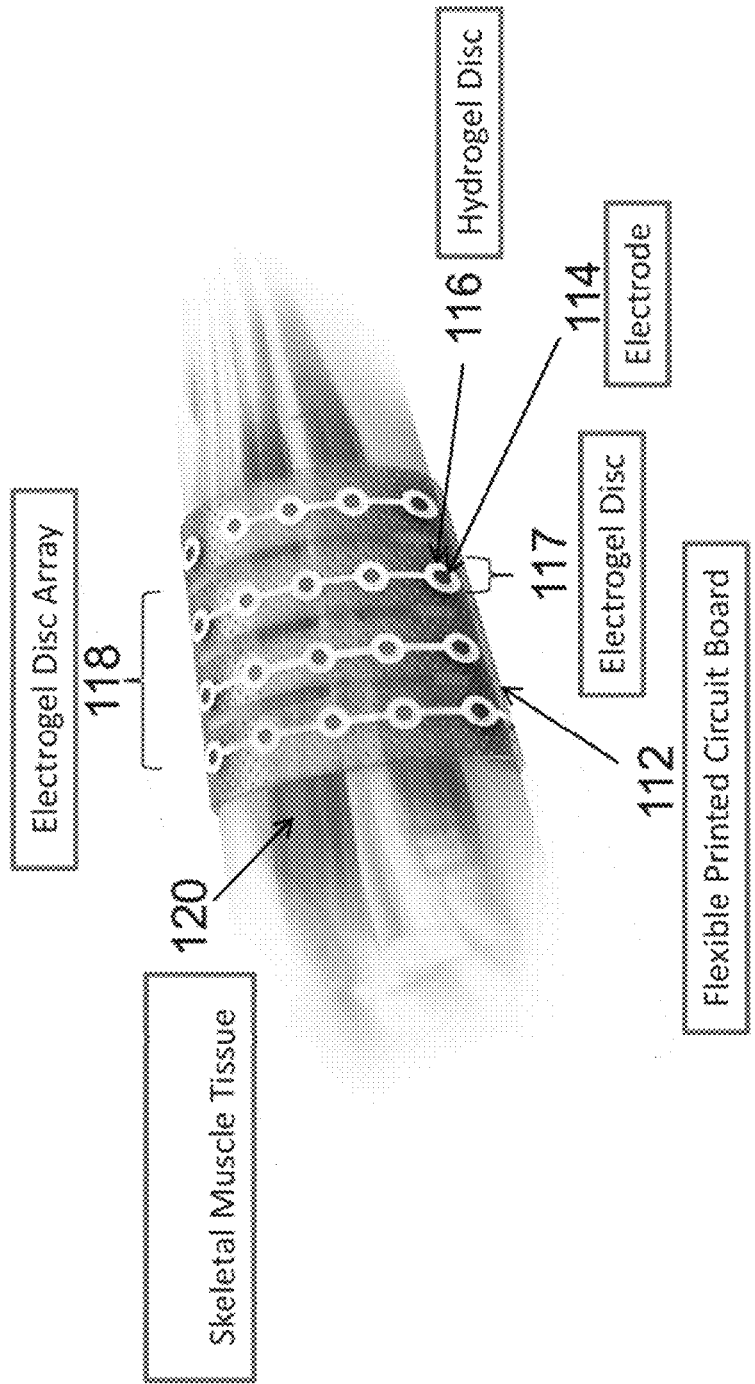
FIG. 2 is a perspective drawing of a previously disclosed neural sleeve, shown in place on a human arm.

FIG. 2 illustrates a neuromuscular stimulation cuff previously disclosed in US20140290451 (PCT Application No. PCT/US2013/073247) which is incorporated herein by reference as if reproduced in full below. The neuromuscular stimulation cuff 110 includes a flexible printed circuit board (PCB) 112 upon which electrodes 114 and hydrogel discs 116 are arranged in an electrogel disc array 118. The neuromuscular stimulation cuff 110 fits over a damaged or degenerative region 120 of the nervous system, e.g. a patient's arm as illustrated. The flexible PCB 112 acts as a substrate upon which the electrodes and other conductive materials are laid. This flexible base layer may be comprised of a single layer of a flexible insulating material, for example a polyimide material. A plurality of electrodes, for example, up to approximately twenty electrodes 114 may be individually etched onto each finger 124 of the flexible PCB 112 as a copper layer. In exemplary embodiments, the flexible PCB 112 has a total of eighty electrodes 114 disposed over four fingers 124. The electrodes 114 may be subsequently plated with a conductive metal such as gold, palladium, or silver for enhanced conductivity.

In some embodiments, electrodes 114 both stimulate a neuromuscular region 120 by stimulating individual muscles and/or groups of muscles, as well as monitor or record skeletal muscle activity, specifically electromyography (EMG) signals. Sensed EMG data pertaining to a sensed muscle target may be used in methods for closed or open loop stimulation of the muscle target. Sensed EMG data may also be analyzed in deciding whether to reposition the neuromuscular stimulation cuff 110 within the neuromuscular region 120 or to turn off individual electrodes 114 within the electrogel disc array 118. Hydrogel discs 116 may be rolled over the electrodes 114 to provide enhanced electrical and mechanical coupling. When appropriately aligned, the hydrogel discs 116 completely cover the electrodes 114 and effectively form conductive electrogel discs 117. Put another way, the electrodes are located between the base layer and the hydrogel discs. Electrical coupling is enhanced in that hydrogel provides greater conductive contact with the skin than is achievable with a bare metal-plated electrode surface. Additionally, a carrier signal provided to any of the electrogel discs 117 in the electrogel array 118 may conduct through the tissues of a patient and be released at any other electrogel disc 117 provided in the array 118. Enhanced mechanical coupling is provided through the exemplary adherence characteristics of hydrogel to the skin. Hydrogel discs 116 may stay coupled to the skin even during complex patient movement. The hydrogel discs are commercially available as a tape which may be rolled on an electrode surface. One such example includes AmGel 2550 from AmGel Technologies. In the exemplary embodiment of the neuromuscular cuff shown in FIG. 4, the hydrogel discs are provided through custom spaced hydrogel discs located on AmGel 2550 rolled hydrogel tape. In the alternative, instead of hydrogel discs, a lotion or discs of a conductive polymer could be used.

The electrogel disc array 118 is spread over a plurality of fingers 124, wherein the fingers 124 are cut from the flexible PCB 112 to provide additional flexibility in the placement of electrogel discs 117. Reanimation of complex motion may require stimulating muscles which are not located directly along the dimensions of a conventionally shaped neuromuscular cuff 110. By wrapping fingers 124 around different muscular regions, e.g. the lower wrist and thumb, complex motions such as thumb movement may be reanimated more effectively than with limited placement options.

Figure 3:
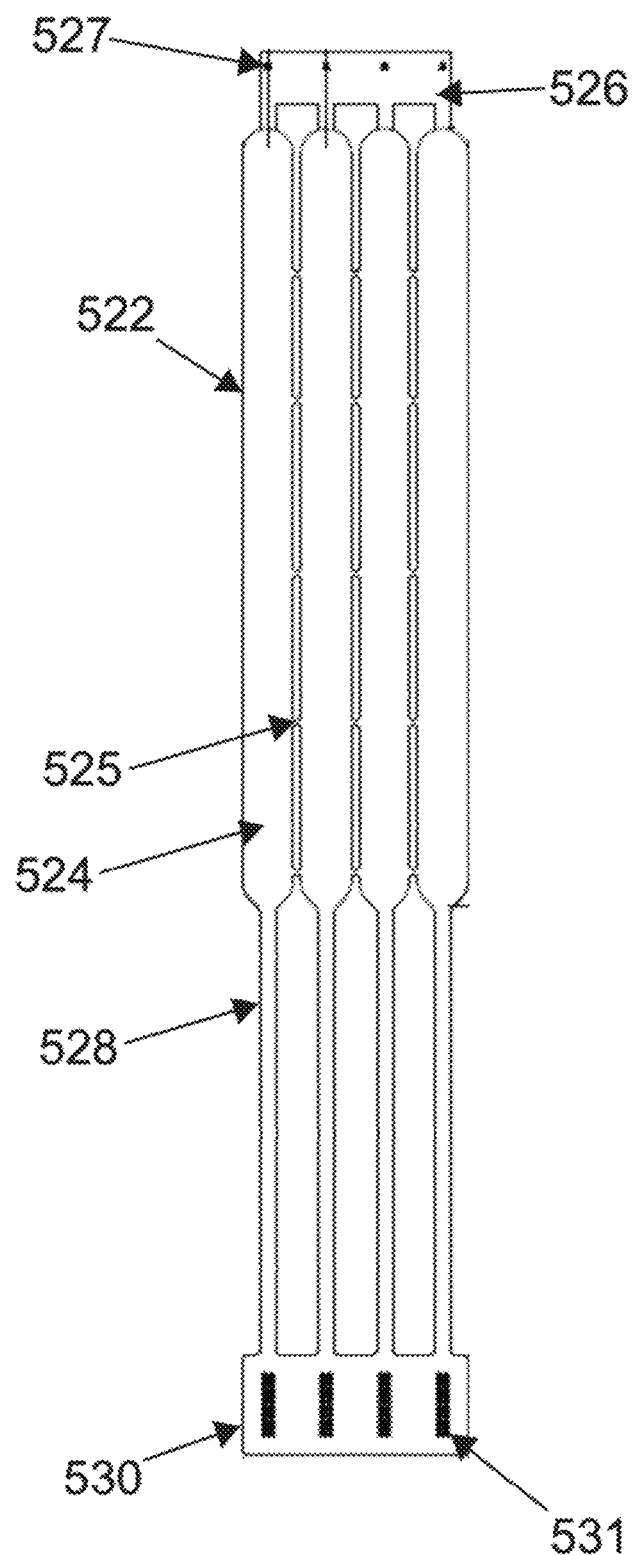
FIG. 3 is a diagram showing the various components of the neural sleeve of FIG. 2.

FIG. 3 shows the neuromuscular cuff/neural sleeve of FIG. 2 laid out in a flat configuration. Dimensions of and between the various components of the design 500 are indicated in millimeters (mm). The design 500 includes, as shown here, an insulating base layer, for example made of a single layer of polyimide base material 522. In some embodiments, the polyimide base material is a DuPont AP8523E polyimide which is 50 μm (micrometers) thick and rolled-annealed copper clad at 18 μm thick. This base material serves as a substrate for the other layers of the neuromuscular stimulation cuff. This base material is formed, for example by cutting, into at least two flexible fingers. As illustrated here, the base material 522 is cut into four fingers 524, where the electrodes will be located or housed. The fingers can be attached to each other, for example by five webbings 525 which run between adjacent fingers.

The fingers 524 extend in the same direction from the rigidizer 530, which acts as a connector for one end of the fingers. In other words, the ends of the fingers distal from the rigidizer are all located in the same direction relative to the rigidizer, or put another way, the rigidizer 530 is at one end of the device. It is noted that the fingers 524 are shown here as extending at a 90-degree angle relative to the connector/rigidizer 530. It is contemplated that the flexible fingers could extend at any angle from the connector 530. Referring back to FIG. 2, setting the flexible fingers at an angle from the rigidizer would permit the flexible fingers to be wound helically around the arm and down along the entire length of the arm.

The rigidizer 530 is used for interfacing with the neural signal processor 104. Drilled holes 531 are additionally located on the rigidizer 530 which represent connector pin insertion points. In exemplary embodiments, eighty drilled holes 531 are approximately 1.016 mm in diameter with a tolerance of +/−0.05 mm. As illustrated here, the fingers 524 are parallel to each other along their entire length. As will be seen later, this is not a requirement.

If desired, an optional fork 526 can be located at the end of the fingers opposite the connector/rigidizer 530. The fork connects all of the fingers, and can be provided for structural support for design and mounting. Drilled holes 527 are provided in the fork 526 for support and/or mounting purposes. In some embodiments, the four drilled holes 527 are approximately 2.387 mm in diameter with a tolerance of +/0.076 mm. Headers 528 extend between the rigidizer and the fingers. These headers are thinner than the fingers, and connect the fingers 524 to the rigidizer 530. The headers are also part of the overall flexible finger, though they are not always required. Though not illustrated, webbings can also be provided between adjacent headers as well if desired. Again, as will be seen later, the fork 526 is optional, though the connector 530 is required.

Figure 4:
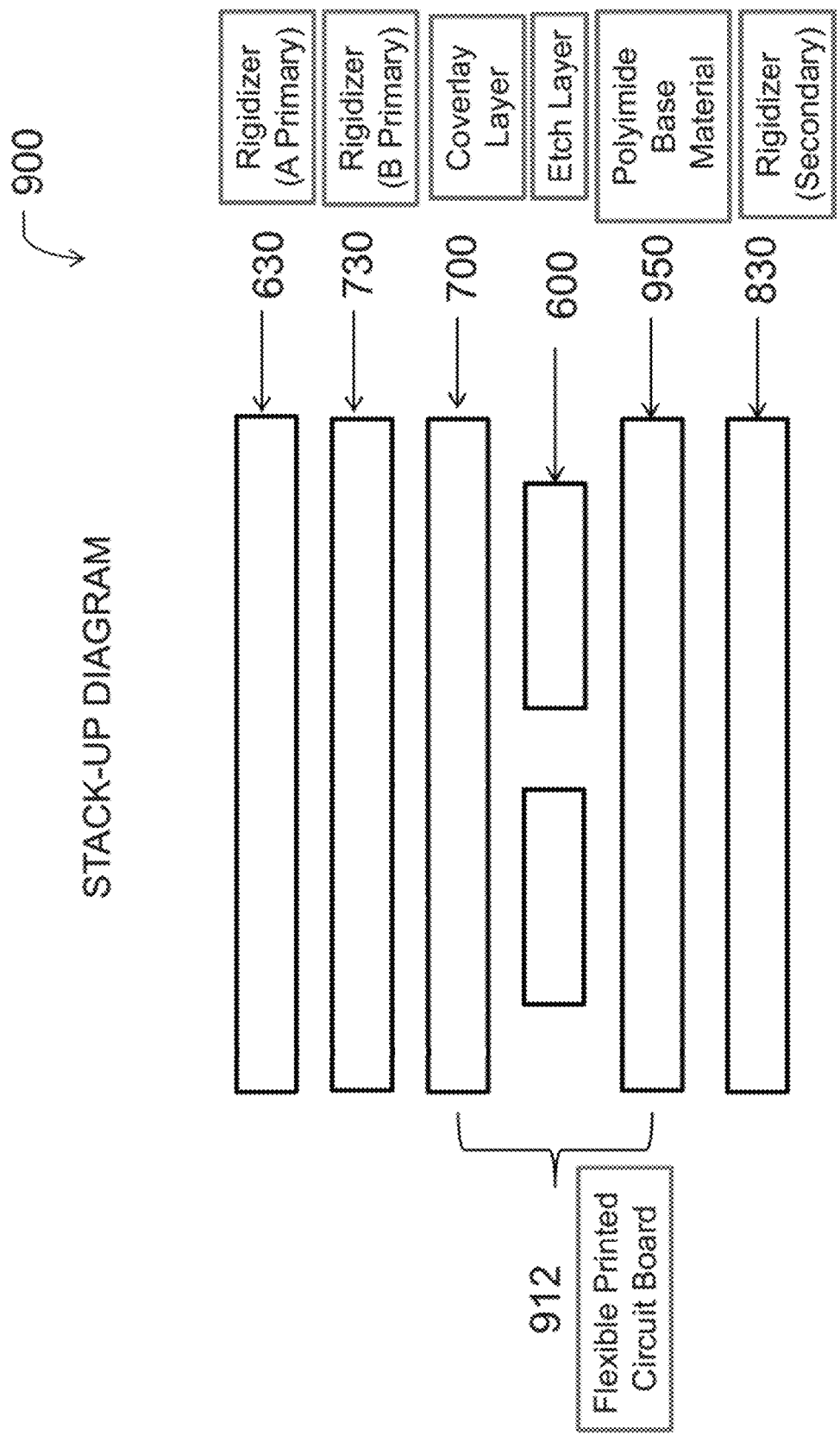
FIG. 4 is a stack-up diagram showing the various layers of the neural sleeve of FIG. 2.

Referring now to FIG. 4, the neuromuscular stimulation cuff device of FIG. 2 and FIG. 3 may be fabricated according to stack-up diagram 900. An insulating base material (e.g. polyimide) provides a substrate 950 upon which various components are fixed. A secondary side rigidizer 830 is laminated to a secondary surface of the substrate 950. The conductive circuit layer 600 is fabricated onto a primary surface of the substrate (opposite the secondary surface), and includes electrodes and traces that form conductive pathways on the flexible base substrate. The coverlay layer 700 is subsequently adhered to the conductive circuit layer 600 which covers the traces and leaves exposed portions of the electrodes. The combination of the substrate 950, conductive circuit layer 600, and coverlay layer 700 is defined as the flexible finger 912. Primary rigidizer 730 is stacked upon the coverlay layer to complete the electrical connection required to interface the flexible finger with the neural signal processor 104.

Figure 5:
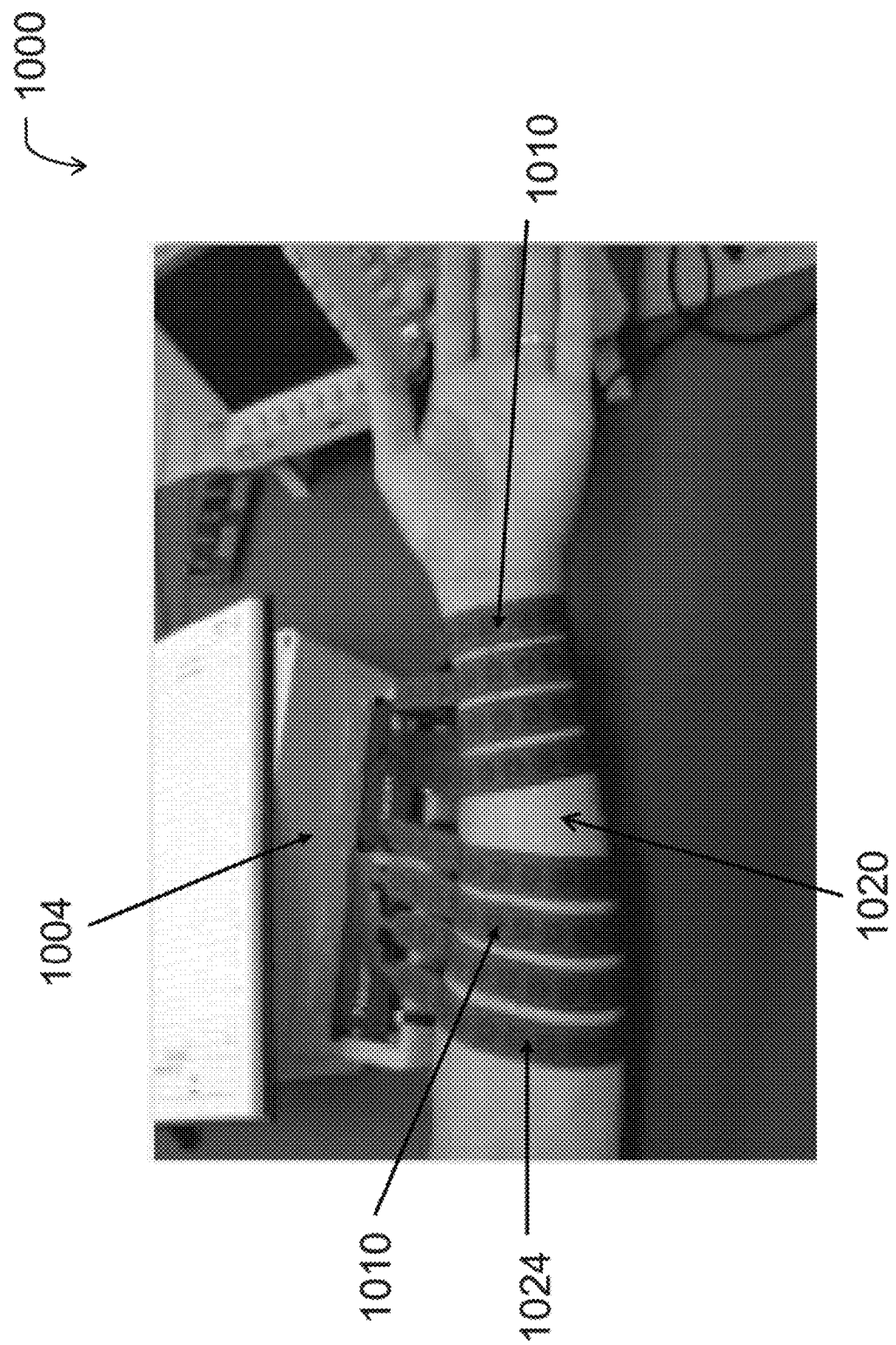
FIG. 5 is an exemplary photograph showing two neural sleeve devices of FIG. 2 on a human arm.

With reference to FIG. 5, two neuromuscular cuff devices 1010 as illustrated in FIGS. 2-4 are shown wrapped around a patient's arm region 1020 in preparation for neuromuscular stimulation. The two cuff devices 1010 together provide 160 separate electrodes for stimulating finger or wrist movements. The flexible fingers 1024 permit the neuromuscular cuff to fit around the arm region 1020 at points of varying circumference. Hydrogel discs 1016 (not shown) keep both cuffs 1010 adhered to the arm.

Figure 6:
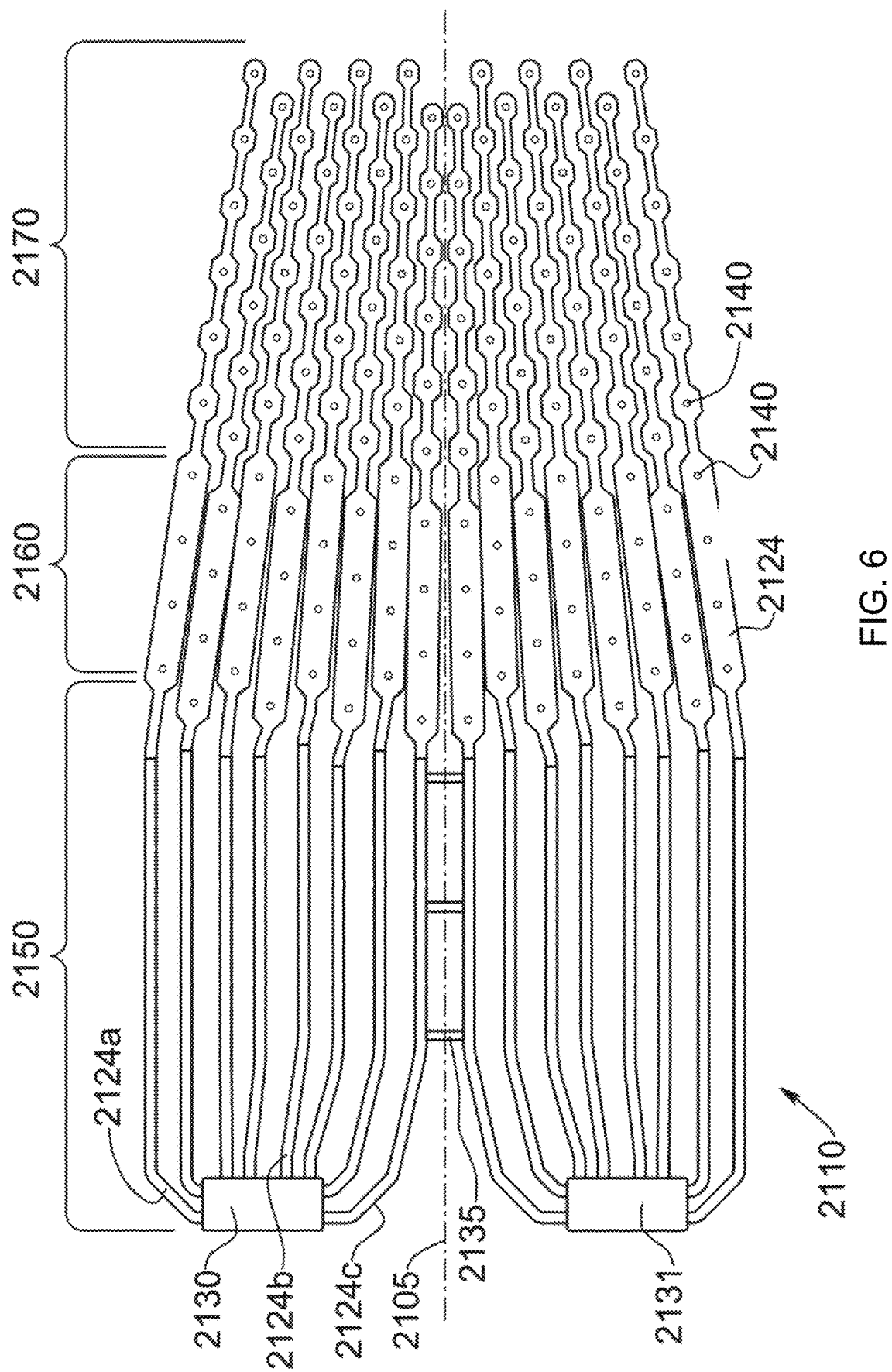
FIG. 6 is diagram of another previously-disclosed neural sleeve. In this embodiment, conductive pathways extend from two different connectors. The fingers extend in the same direction, and taper towards a center axis.

In another exemplary embodiment, the flexible fingers of a neural sleeve 2110 do not need to be straight for their entire length. Referring now to FIG. 6, flexible fingers 2124 extend from first connector 2130, which has a rectangular shape in this illustration. The flexible conductive pathways 2124 in this embodiment "change" directions as they extend from connector 2130. For example, an upper flexible finger 2124a first extends upwards from the connector 2130, then changes direction so that its electrodes 2140 are to the right of the connector 2130. A center flexible finger 2124b extends from the right-hand side of the connector 2130 off to the right of the connector. A lower flexible finger 2124c first extends downwards from the connector 2130, then changes direction so that its electrodes 2140 are also to the right of the connector 2130. Notably, none of the electrodes 2140 are present to the left of the connector 2130.

This embodiment of a neural sleeve 2110 also contains more than one connector I rigidizer. As illustrated here, the neural sleeve 2110 has a first connector 2130 and a second connector 2131. Flexible fingers extend in the same direction (here, to the right) of both connectors. Webbings 2135 connect flexible fingers extending from each connector 2130, 2131. There may be any number of webbings 2135, and the webbings 2135 may connect the flexible fingers at any portion of their length. Here, the webbings 2135 are present along a non-electrode-containing portion 2150 of the flexible fingers (i.e. the header portion). Though not depicted, it is specifically contemplated that the flexible fingers of one connector 2130 may be of a different length from the flexible fingers of the other connector 2131.

The electrodes 2140 may be evenly spaced apart along the length of the flexible fingers 2124, or their spacing may vary, for example becoming shorter or longer, as the distance from the connector 2130 increases. For example, muscle segments get smaller closer to the wrist, so the electrodes need to be closer together as well. However, the electrodes do not need to be present along the entire length of the flexible fingers. As seen here, the flexible fingers 2124 may include a non-electrode-containing portion 2150 extending from the connector, which is similar to the header 528 of the embodiment of FIG. 3. The flexible finger may also include a non-scalloped electrode-containing portion 2160, and a scalloped electrode-containing portion 2170 at the distal end of the flexible finger (i.e. distal from the connector). It should be noted that none of the flexible fingers overlap with each other.

The electrode-containing portions 2160, 2170 of the flexible fingers have a different shape from each other. One reason for this difference in shape is because, as seen here, the distal ends of the flexible fingers 2124 extend inwardly towards a center axis 2105 of the neural sleeve 2110. Put another way, the flexible fingers 2124 taper inwards towards the center axis 2105. The scalloped portions 2170 of adjacent flexible fingers permit them to fit into a smaller area while still providing a suitable number of electrodes (note the electrodes do not change in size). However, the flexible fingers 2124 all still extend in the same direction away from the connector 2130, i.e. to the right in this figure. Put another way, the flexible fingers comprise a first portion which is transverse to the center axis 2105, and a second portion which is parallel to the center axis. These portions are particularly seen in the flexible finger 2124a, which first extends upwards (i.e. transversely to the center axis), then extends parallel to the center axis.

This particular embodiment is intended to be used on a patient's arm with the two connectors 2130, 2131 located near the shoulder, and the scalloped portions 2170 near the wrist and hand.

The neural sleeves of FIGS. 2-6 are contemplated to be used in the form of an inner sleeve. An outer sleeve could be made of a flexible, stretchy, and/or compressible fabric material which would press the inner sleeve snugly against the user's body (e.g., arm). The material could also be a dry-fit material, i.e. a material which can move sweat away from the user's arm and permit the sweat to evaporate. It is noted that the flexible fingers of these neural sleeves generally do not provide great mechanical support.

In these embodiments of FIGS. 2-6, the neurostimulation sleeve includes electrodes attached to an electrical circuit. The circuit is then secured to the patient by adhesion of hydrogel electrodes to the skin or by another sleeve surrounding the circuit. The electrodes are electrically isolated from each other by air between them. How the neurostimulation sleeve fits the patient is critical to ensure adequate pressure is applied to the electrodes, as well as to provide proper electrode coverage over the limb. Due to the variability of limb sizes (e.g. diameter, shape, length, etc.), it is desirable to have a stimulation system that can quickly and easily adapt to different limb dimensions. Battelle Memorial Institute's PCT Application WO 2016/196801 and the corresponding US priority provisional patent application 62/169,849 are incorporated herein as if reproduced in full below.

In order to provide a better fit with variable lengths, diameters, and shapes, a flat, flexible sheet can be embedded with electronics and connecting wires. These components can be cast in the sheet and laid out to provide the ability to cut off excess material depending on the size and shape of the treatment area of the patient. Generally, the flexible sheet comprises a non-conductive flexible substrate, a plurality of electrodes embedded within the flexible substrate, and electrically conductive wires running through the flexible substrate from a common exterior surface to each electrode.

Figure 7:
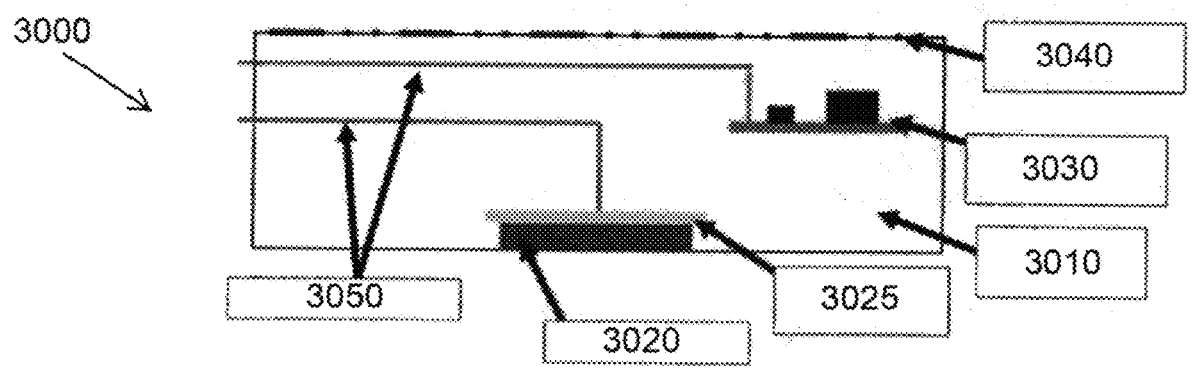
FIG. 7 is a cross-sectional schematic view of a flexible sheet used to make neural sleeves in accordance with some embodiments of the present disclosure.

FIG. 7 is a cross-sectional view of an exemplary embodiment of such a flexible sheet. The sheet 3000 includes a flexible substrate 3010. This substrate can be formed from an elastomeric polymer, and should be non-conductive. If desired, insulating ceramic material can be dispersed throughout the substrate. Electrodes 3020 are present along a bottom surface of the flexible substrate 3010. Other embedded sensors or other electronics (e.g., accelerometers, bend sensors) 3030 can also be embedded within the flexible substrate. Wires 3050 connect the housed/embedded components to an exterior surface of flexible substrate 3010. The wires of different embedded electrodes/sensors all run to the same exterior surface, i.e., the common exterior surface. It is contemplated that the flexible sheet can be cut to size, and this permits the wires to be avoided during cutting. Some wires may be cut when the sheet is cut to size; however, since the wires all run to a common exterior surface, conductivity to the electrodes is maintained. In some preferred embodiments, the flexible substrate comprises holes 3195 that allow for air and moisture to pass through the sheet 3100.

The electrode 3020 is made of a conductive polymer or a metal. A charge dispersing plate 3025 can be placed between the electrode 3020 and the wire 3050. This is used to properly disperse the charge from the wire to the conductive polymer used for stimulation. Optionally, a conduction enhancer is present on the exterior surface of the electrode.

The electrically conductive wires 3050 may be insulated or bare. The wires 3050 may be suspended and cast in the flexible substrate 3010. The ends of the wires 3050 may extend out of the substrate 3010, or a connection may be used to penetrate the substrate 3010 and connect to the wires 3050.

Aside from the depicted components, other elements may be suspended in the substrate 3010 in order to provide mechanical security, electrical insulation, and/or tamper protection. This includes accelerometer 3030.

The substrate can include a label 3040 printed on an exterior surface, which may allow for serialization, branding, or assembly and use instructions to be provided on the device 3000. The label 3040 may be masked or printed on the substrate 3010. In some embodiments, pigmented components can be cast in place to provide contrasting elements.

The substrate 3010 may rely on the dielectric strength of the elastomeric polymer to limit the distance a charge can travel in order to prevent the charge from shorting between electrodes or throughout the whole sheet. To prevent conductivity on any exterior surface of the sleeve, a mask or mold coating can be used. When joining different polymers (e.g. the wires are also made of a conductive polymer), a manufacturing method should be used that promotes polymer chain diffusion and subsequent entanglement to ensure that the flexible sheet is mechanically secure.

The embedded components may be located within/on the flexible sheet in a pattern such that the sheet can be cut to best fit the patient in such a manner to maintain electrical continuity for the concerned stimulation area while cutting off unnecessary portions of the flexible sheet (i.e., in the case of a smaller diameter arm). If a conductive portion of the sheet is cut, the edges may be coated in an insulating film and the partial conductive surfaces may be excluded from stimulation. The sensors and other electronics may be embedded at locations in the sheet to minimize the likelihood of intersecting the cutting lines.

Figure 8:
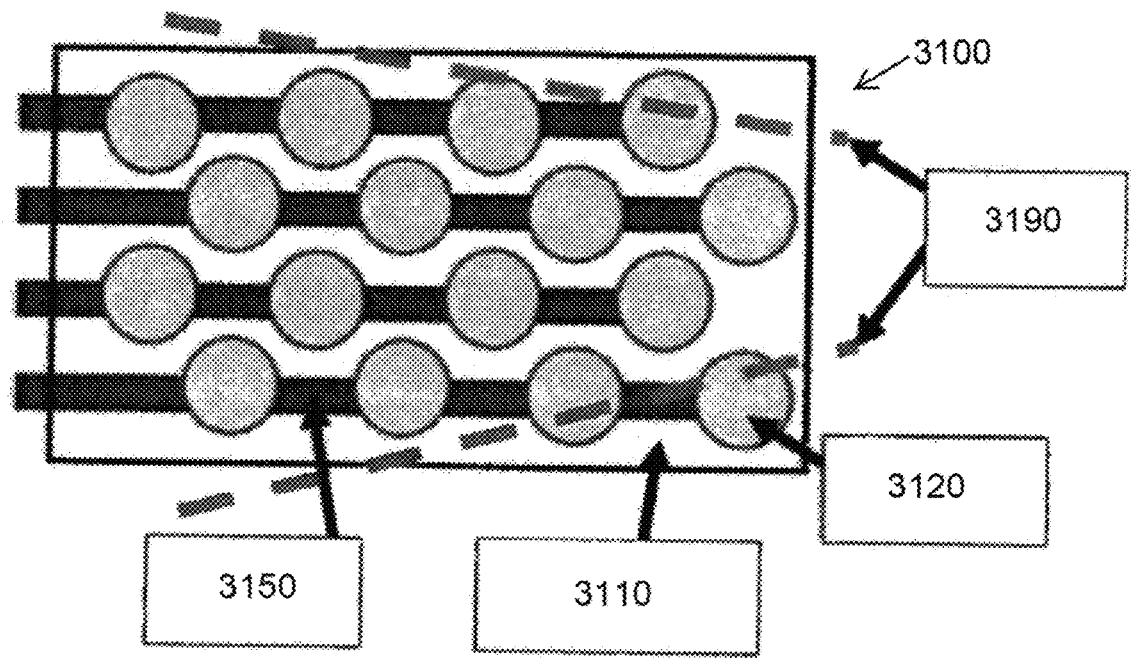
FIG. 8 is a schematic view of cutting lines that can be used to fit the flexible sheet into a neural sleeve of appropriate size for a given user.
Figure 9:
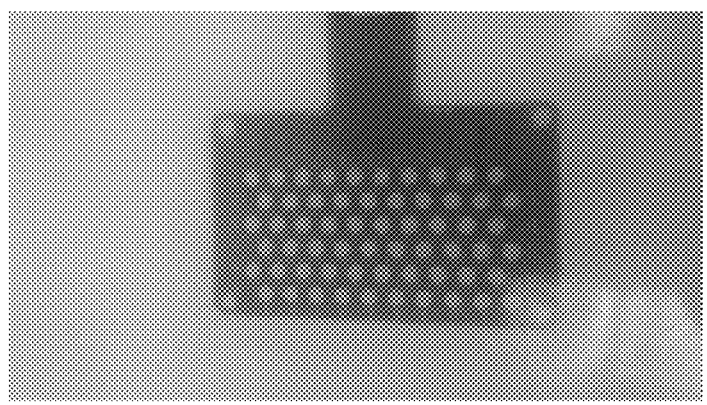
FIG. 9 is a photograph showing a rigidizer with holes drilled for connection insertion points. The rigidizer is embedded in a silicone matrix.
Figure 10:
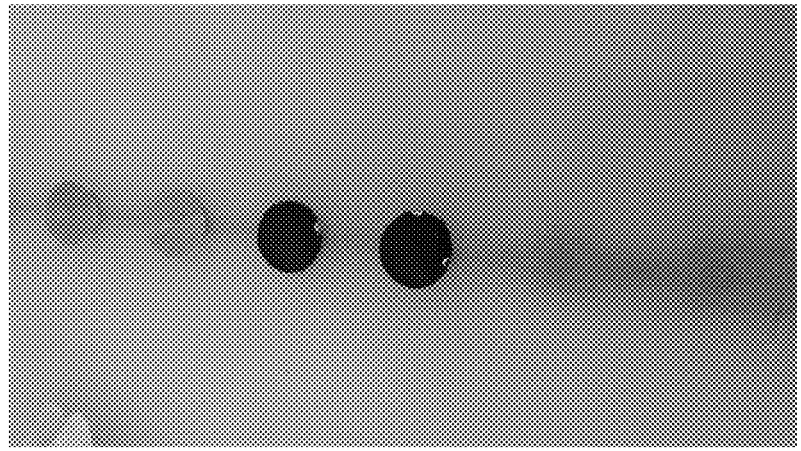
FIG. 10 is a photograph showing electrodes embedded in a silicone matrix. The black electrodes have a conductive coating over the exposed surface of the metal electrode.
Figure 11:
FIG. 11 is a photograph of a sleeve with electrodes and electrical connections embedded in a silicone matrix.

FIG. 8 is a top view of an exemplary embodiment of a flexible sheet. The sheet 3100 includes non-conductive elastomer portions 3110, electrodes 3120, and wires/flex bundles 3150. Each row of electrodes is connected to common electrically-conductive wires that are not shared by the other rows of electrodes. The dashed lines represent potential cutting lines 3190 for customizing the size and shape of the substrate 3100 to match a treatment area on a patient.

The flexible sheet 3100 could be made by fixing the electrodes, optional embedded sensors 3030 and electrical connections 3050, and then adding (e.g., pouring) an elastomeric polymer or polymeric precursor that is cured to form matrix 3010. Optional holes 3195 could be created by using rods or pins around which the matrix would at least partially cure and removing the rods or pins to leave holes to enhance breathability. Typically, the elastomeric polymer or polymeric precursor poured over the various components onto a release surface such as a release liner (for example paper coated with a fluoropolymer) or a nonstick mold. After removing from the mold or removing the release liner, the electrode surfaces are exposed. Subsequently, for better skin contact, the electrodes can be coated or made entirely with a conductive polymer that could be, for example, a polymer composite comprising conductive carbon or metal particles (typically silver or copper). Alternatively, the electrodes can be coated with a conductive interface prior to adding the elastomeric polymer or polymeric precursor. For example, a conductive polymer is applied over the electrodes (that can be fully or partially cured) prior to applying the matrix elastomer. In another alternative, the bottom surface (i.e., the surface to be contacted with the skin) has an uncured or partly cured polymer layer and the areas in contact with the electrodes is injected with a conductive material. Desirably, the portion of the electrode that is on the bottom surface (the surface contacting the skin) is a conductive polymer.

The elastomer is a soft material having a Shore A Hardness (ASTM D2240) of 70 or less, preferably 60 or less, more preferably 50 or less. The elastomer may be, for example, silicone (examples of commercially available silicones include Ecoflex® 00-30, Dragon Skin® 30), polyurethane, and rubber. Since even flexible printed circuit boards lack ideal flexibility and softness, in some preferred embodiments, the sleeve comprises at least 50 mass % or at least 70 mass % elastomer; desirably the elastomer forms a matrix through the entire thickness of the sleeve with all components embedded within the matrix except (in some cases) the bottom surface of the electrodes. The system that utilizes a combination of electrodes and sensors within the elastic sleeve creates synergistic advantages in motion control, especially in the case of an elastomeric matrix that keeps the components fixed with respect to each other.

The flexible sheet may also contain magnets, for example magnetic strips that mate when the sheet overlaps. Mechanical fasteners can be embedded into the elastomeric polymer or polymeric precursor. The electrical connections can be wires that are soldered to the electrodes. Typically, each electrode is connected to one wire and is separately addressable. The electrical connections through the matrix to the electrodes may also be achieved via printed circuit boards (including flex circuit boards) that are suspended in the matrix elastomer.

The substrate could be an elastic fabric or could be a flexible fabric that is coated by an elastomer. In a preferred embodiment, the fabric is a mesh that is coated by an elastomer and, in the cured form, holes remain in the sheet so that the sheet is breathable. The electrodes can be embedded in the fabric, or the flexible fabric forms a backing material that is bonded to, and provides structural support for, the elastomeric sheet.

The sheet is configured so that the electrical connections are all on one side of the sheet. In this fashion, the sheet can be wrapped around a limb and cut to size; thus forming a custom-sized device for each person.

After the substrate has been cut to the desired size, various methods can be used to join opposing edges of the flexible sheet together to form a sleeve. In some embodiments, a compression sleeve may hold the cut flexible sleeve against the skin of a patient. In other embodiments, the attachment may be made using a part of the sheet. Non-limiting examples include embedding a mechanical fastener (e.g., a snap button, a hook and loop fastener, a zipper, or a magnet) into the flexible sheet or applying a low-tack adhesive to the sheet. The mechanical fastener may be patterned similarly to the stimulation pads and electronics to allow for various sizes. The low-tack adhesive may be used to secure the flexible sheet material to itself.

In other embodiments, the conductive and non-conductive components may be printed onto a fabric substrate via additive manufacturing (i.e., 3D printing). Additive manufacturing allows printing to the custom size of the patient.

Alternatively, metals may be deposited, sewn, or otherwise attached directly to the fabric instead of being embedded in a casting. High-gauge wires (insulated or bare) may be woven into a custom sleeve. The sleeve may be made to a desired size or post-processed to fit the patient. In another alternative, the components can be incorporated into a fabric substrate by 3D weaving techniques.

The neural sleeve can incorporate several different types of sensors to provide information on data and feedback on the position and movements of the limb and other body parts. For example, desired position information from the sensors can include a 3-dimensional location (X, Y, Z coordinates) of various points on the hand and arm relative to the body and to each other, and rotation information of the wrist, elbow, and shoulder relative to the body. Orientation of various body parts with respect to gravity can also be measured with an accelerometer (or inclinometer). Motions of the hand and arm may be derived from position sensors or from independent sensors. Other desired information includes joint angles at the elbow, wrist, thumb and fingers (or other body joints). A variety of concepts for sensors may be used to measure one or more of these data items. Broad categories of sensors include accelerometers, micro-electro-mechanical (MEMS), electronic (based on resistance, capacitance, or resonance), fluid bladders, optical fiber bend sensors, and video tracking systems. Again, these concepts can be generally applied to a neural sleeve on any body part or limb (e.g. arm, hand, leg, foot, etc.).

The neuromuscular sleeve/neural sleeve could be operated in a wireless, battery-operated mode. In this case, the battery pack and the electronics module can be strapped on the upper arm of the subject in the form of an arm band. The device can be connected to the user's mobile device and/or PC for data transfer and real time tracking/monitoring.

It will further be appreciated that the disclosed techniques may be embodied as a non-transitory storage medium storing instructions readable and executable by a computer, (microprocessor or microcontroller of an) embedded system, or various combinations thereof. The non-transitory storage medium may, for example, comprise a hard disk drive, RAID or the like of a computer; an electronic, magnetic, optical, or other memory of an embedded system, or so forth.

The inventive sleeve can also be cooled for greater patient comfort. The sheet could contain a material with a high thermal capacity. This material could be mixed into the non-conductive potting (matrix) material in order to hold the temperature better. The sleeve could then be put in the freezer like an ice pack (in fact, the material could be water stored in packets within the sleeve). In addition to keeping the arm cool, this could help reduce inflammation or swelling while the system is being used. A longer-duration approach would be active cooling, which could be done by passing a coolant through a flexible tube embedded in the elastomer. This could function similarly to water-cooled computer hardware.

In one prototype, a medical grade silicone material was used for the non-conductive potting material. Because of the surface energies of the silicone and the polyimide (amber-colored flex-circuit material), the adhesion was poor. A material change to a more adhesive material such as urethane would improve structural integrity. A surface treatment, like corona or plasma treatments (for example, corona or plasma treatments to all or part of the polyimide surface prior to embedding in an elastomer) could also modify the material and result in improved adhesion with a silicone or other elastomer. In some embodiments, flow holes in the circuit board could provide mechanical interlocking.

The printed circuit board is typically flexible; flexible electronics are a well-known class of circuits. For the present invention, these can be attached to a fabric substrate. In some embodiments, the fabric is embedded into an elastomer and, particular where the fabric is a mesh fabric, the neural sleeve is breathable. Embedding a fabric into an elastomer provides better mechanical strength. Also, by embedding fabric within the elastomer, more fastening opportunities can be created.

Instead of a flexible circuit board, simple wires could be used and wires could be woven into a fabric; for example conductive wires woven into an insulating fabric which could be natural or synthetic fibers. The wires could be connected to electrodes.

In addition to neuromuscular stimulation, it could be used in other applications for a conformal sheet containing electronics or electrodes. The electrodes in the present invention can use electrogel discs or other conductive medium.

In another aspect, the electrodes (or sensors or other components) are dispersed throughout a sheet (for example, equally dispersed) and connected to wires which are connectable to an interface. With this composite sheet, the sheet can be cut to any desired size, wrapped around a body part, fastened in place and the wires can be connected to an interface. Thus, the invention is customizable to each type of application (leg, arm, etc.) and each individual.

The invention also includes methods of treatment using any of the devices described herein to transmit electrical signals between the skin and an interface to a computer. For example, the invention includes a method for thought controlled neuromuscular stimulation using the steps described in the incorporated patent using the device described herein.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of making a flexible sheet, comprising:
   in a mold, placing conductive wires in connection with electrodes or in connection with contacts for electrodes;
   adding an elastomer precursor into the mold to encase the conductive wires and the electrodes or to encase the conductive wires and the contacts for electrodes;
   wherein a release liner is disposed between the mold and the elastic precursor; and
   curing the elastomer precursor to create the flexible sheet with embedded wires and electrodes or contacts for electrodes.

2. The method of claim 1 wherein contacts for electrodes that are individually connected to conductive wires are placed in the mold; and
   after the elastomer precursor is added to the mold; further comprising a step of making electrodes by placing a conductive polymer in contact with the contacts for electrodes.

3. The method of claim 2 wherein the step of making electrodes comprises adding conductive particles to the uncured elastomer precursor to make the electrodes.

4. The method of claim 2 wherein the step of making electrodes comprises depositing a precursor for a conductive polymer in contact with the contacts for electrodes.

5. The method of claim 4 wherein the conductive polymer is colored differently from the elastomer that makes the sheet.

6. The method of claim 1 wherein a sensor is placed in the mold prior to adding the elastomer precursor.

7. The method of claim 6 further comprising a fastener embedded in the elastomer precursor for forming a sleeve.

8. The method of claim 7 wherein the fastener comprises a snap button, a hook and loop fastener, a zipper, or a magnet.

9. The method of claim 6 wherein the sensor comprises an accelerometer.

10. The method of claim 1 wherein the electrodes are made with polymers comprising conductive carbon or metal particles.

11. The method of claim 1 wherein the elastomer has a Shore A Hardness of 60 or less.

12. A method of making a flexible sheet, comprising:
in a mold, placing conductive wires in connection with electrodes or in connection with contacts for electrodes;
adding an elastomer precursor into the mold to encase the conductive wires and the electrodes or to encase the conductive wires and the contacts for electrodes; and
curing the elastomer precursor to create the flexible sheet with embedded wires and electrodes or contacts for electrodes; and
wherein holes are created in the flexible sheet by using rods or pins around which the elastomer precursor would at least partially cure and removing the rods or pins to leave the holes; and
wherein the electrodes are made with polymers comprising conductive carbon or metal particles.

13. The method of claim 12 wherein a release liner is disposed between the mold and the elastic precursor.

14. The method of claim 12 wherein the mold is a nonstick mold.

15. A method of making a flexible sheet, comprising:
in a mold, placing conductive wires in connection with electrodes or in connection with contacts for electrodes;
adding an elastomer precursor into the mold to encase the conductive wires and the electrodes or to encase the conductive wires and the contacts for electrodes; and
curing the elastomer precursor to create the flexible sheet with embedded wires and electrodes or contacts for electrodes; and
wherein an uncured or partly cured polymer layer is injected with a conductive material.

16. A method of making a flexible sheet, comprising:
in a mold, placing conductive wires in connection with electrodes or in connection with contacts for electrodes;
adding an elastomer precursor into the mold to encase the conductive wires and the electrodes or to encase the conductive wires and the contacts for electrodes; and
curing the elastomer precursor to create the flexible sheet with embedded wires and electrodes or contacts for electrodes; and
wherein the sheet comprises at least 50 mass % elastomer;
wherein an elastic fabric or a flexible fabric is coated by the elastomer.

17. The method of claim 16 wherein the elastic or flexible fabric is a mesh.

* * * * *